US010288910B2

(12) United States Patent
Fayolle et al.

(10) Patent No.: US 10,288,910 B2
(45) Date of Patent: May 14, 2019

(54) DEVICES AND METHODS FOR DETERMINING THE POSITION OF A CHARACTERIZING POINT OF AN EYE AND FOR TRACKING THE DIRECTION OF THE GAZE OF A WEARER OF SPECTACLES

(71) Applicant: ESSILOR INTERNATIONAL (COMPAGNIE GENERALE D'OPTIQUE), Charenton-le-pont (FR)

(72) Inventors: Romain Fayolle, Charenton-le-Pont (FR); Sylvain Chene, Charenton-le-Pont (FR)

(73) Assignee: ESSILOR INTERNATIONAL Charenton-le-Pont (FR)

( * ) Notice: Subject to any disclaimer, the term of this patent is extended or adjusted under 35 U.S.C. 154(b) by 0 days.

(21) Appl. No.: 15/526,346

(22) PCT Filed: Nov. 14, 2014

(86) PCT No.: PCT/FR2014/052919
§ 371 (c)(1),
(2) Date: May 12, 2017

(87) PCT Pub. No.: WO2016/075372
PCT Pub. Date: May 19, 2016

(65) Prior Publication Data
US 2017/0322430 A1 Nov. 9, 2017

(51) Int. Cl.
*G02C 13/00* (2006.01)
*A61B 3/113* (2006.01)
(52) U.S. Cl.
CPC ............ *G02C 13/005* (2013.01); *A61B 3/113* (2013.01)

(58) Field of Classification Search
CPC .............................. G02C 13/005; A61B 3/113
(Continued)

(56) References Cited

U.S. PATENT DOCUMENTS

| 7,572,008 B2 | 8/2009 | Elvesjo et al. |
| 9,028,068 B2 | 5/2015 | Chang |

(Continued)

FOREIGN PATENT DOCUMENTS

| CN | 1725976 | 1/2006 |
| CN | 103748599 | 4/2014 |

(Continued)

OTHER PUBLICATIONS

International Search Report, dated Jul. 27, 2015, from corresponding PCT application.

*Primary Examiner* — Tuyen Tra
(74) *Attorney, Agent, or Firm* — Young & Thompson

(57) ABSTRACT

The invention relates to a device for determining the position of a characterizing point of an eye of a wearer provided with a spectacle frame (400), including: at least one image sensor apparatus (120); and positioning element for positioning the image sensor device relative to the spectacle frame (400), such that, when the spectacle frame is arranged in a useful position on the head of the wearer, the image sensor apparatus is capable of capturing an image of the eye of the wearer; and element for determining the position of a characterizing point of the eye from the at least one image of the eye of the wearer captured by the image sensor apparatus. The invention also relates to a method for determining the position of a characterizing point of an eye of a wearer, a device and a method for determining the direction of the gaze and a method for determining associated areas of wear of an ophthalmic lens.

23 Claims, 3 Drawing Sheets

Figure 5:
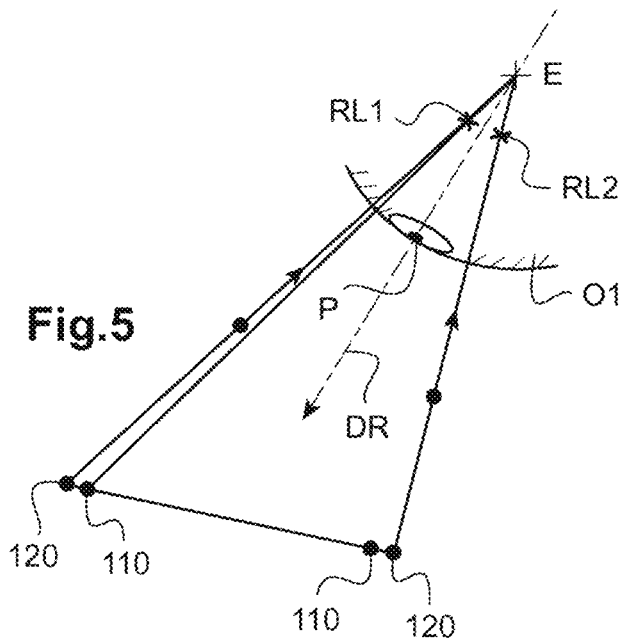

(58) Field of Classification Search
USPC .................................................. 351/200, 204
See application file for complete search history.

(56) References Cited

U.S. PATENT DOCUMENTS

| | | |
|---|---|---|
| 9,931,069 B2 | 4/2018 | Publicover et al. |
| 2010/0195045 A1 | 8/2010 | Nauche et al. |
| 2012/0025716 A1 | 10/2012 | Encaua et al. |
| 2014/0009739 A1 | 1/2014 | Greco et al. |
| 2015/0002807 A1 | 1/2015 | Haddadi |
| 2015/0286070 A1 | 10/2015 | Aikawa |

FOREIGN PATENT DOCUMENTS

| | | |
|---|---|---|
| CN | 103777351 | 5/2014 |
| EP | 0 125 808 A2 | 11/1984 |
| WO | 2011/042623 A1 | 4/2011 |
| WO | 2013/121128 A1 | 8/2013 |
| WO | 2014/046206 A1 | 3/2014 |

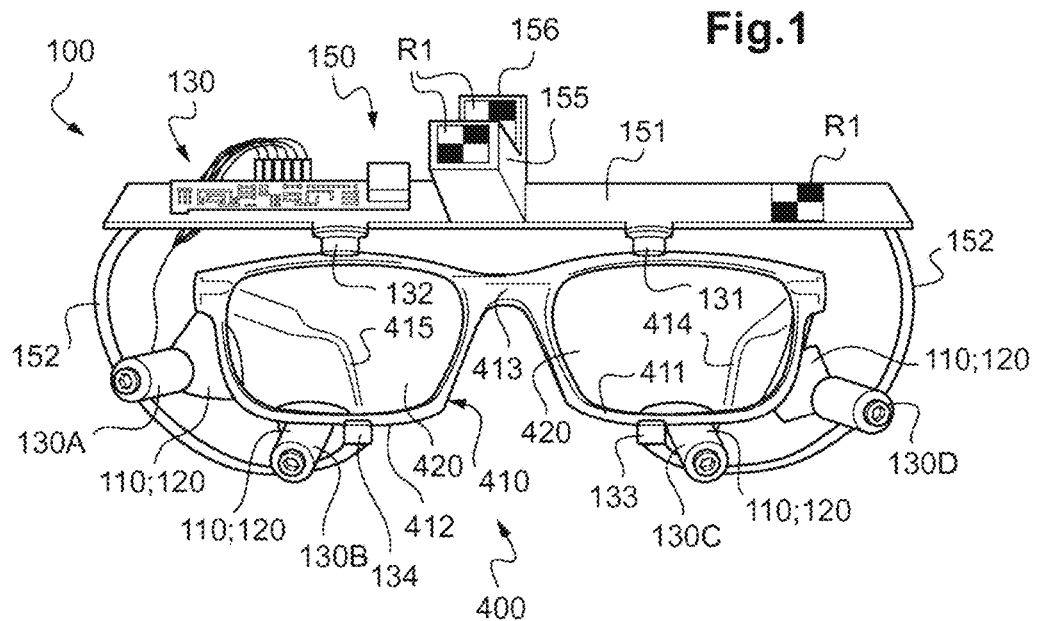
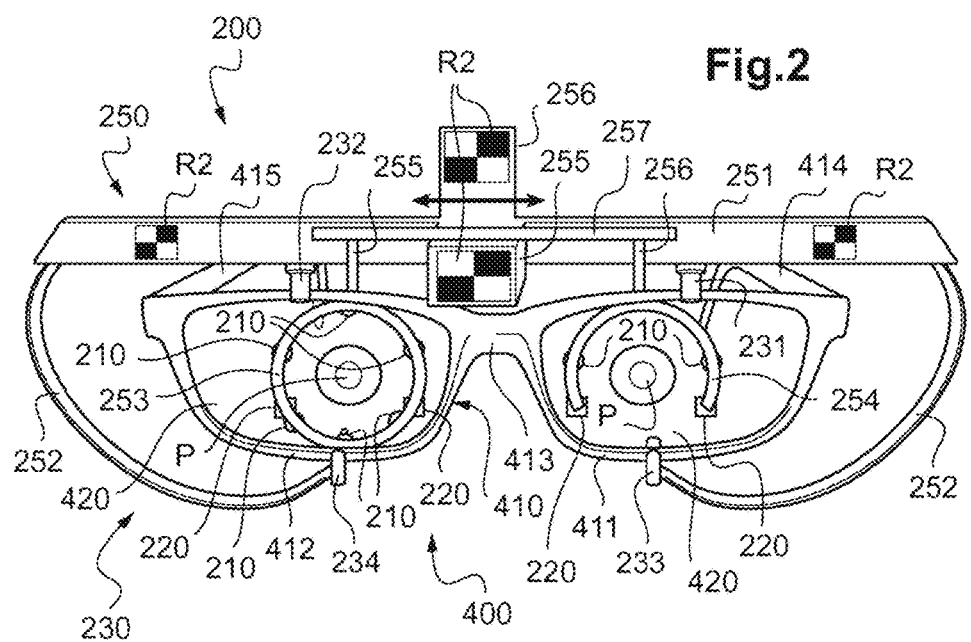

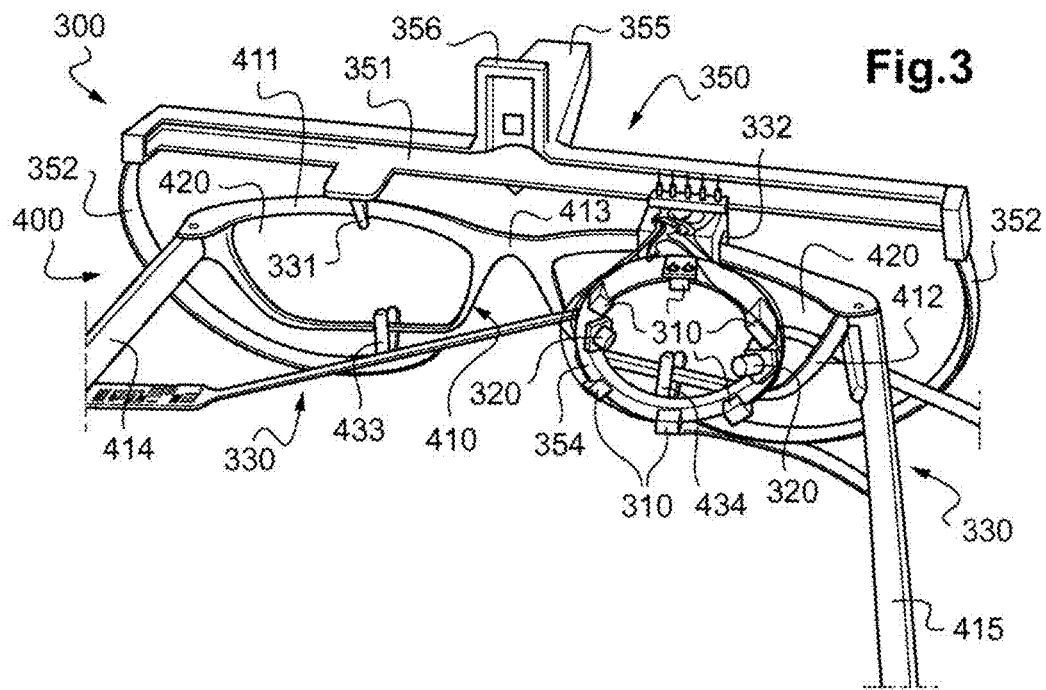
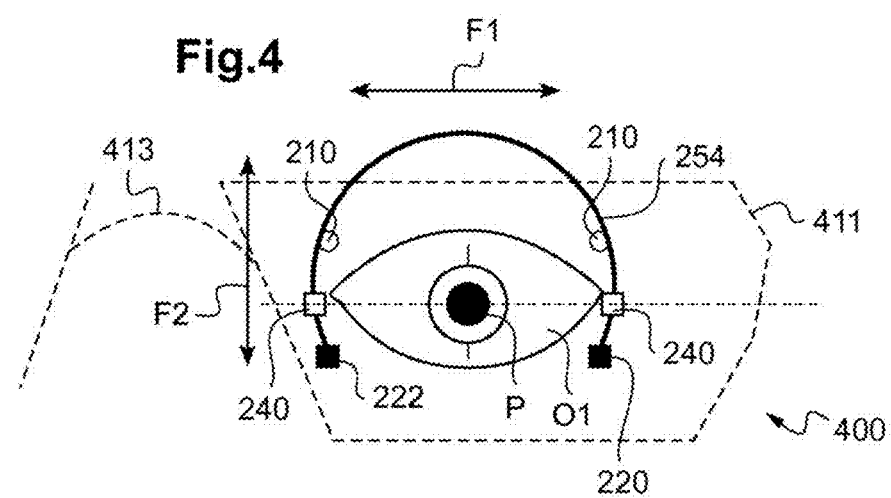

DEVICES AND METHODS FOR DETERMINING THE POSITION OF A CHARACTERIZING POINT OF AN EYE AND FOR TRACKING THE DIRECTION OF THE GAZE OF A WEARER OF SPECTACLES

TECHNICAL FIELD OF THE INVENTION

The present invention generally relates to the field of devices and methods for determining the position of a noteworthy point of an eye of an individual and to devices and methods for tracking the gaze direction of an individual.

One particularly advantageous application thereof is to the implementation of a method for determining zones of use of ophthalmic lenses for a wearer of a vision frame.

TECHNOLOGICAL BACKGROUND

It is sought, in the context of the design of personalized ophthalmic vision-correcting lenses, to take into account individual geometrico-postural parameters of the wearer (referred to as personalized optical design parameters) and the frame he has chosen.

The sought-after geometrico-postural parameters are related not only to the geometry of the head of the wearer and to that of the chosen spectacle frame, but also to the posture of the wearer and to his visual behavior.

In order to determine these parameters, the values of the following quantities are in particular determined: height of the eyes of the wearer with respect to the lower edge of the lens or of the spectacle frame, interpupillary distance, position of the eye rotation centers, eye-head coefficient (i.e. the ratio between the angle of rotation of the head and the angle of rotation of the eyes during the reading of a text, or more generally, during a visual stimulus that is off center with respect to a reference visual axis corresponding to a straight-ahead gaze direction), value of the "inset" for a progressive ophthalmic lens, distance between the back face of the ophthalmic lens and the top of the cornea of the eye.

"Inset" is defined in the standard ISO13666: 2012 as the horizontal distance between the fitting cross and the center of the designed near zone. "Inset" is also called "internal offset". It depends on the visual behavior of the wearer.

Ophthalmic progressive lenses allow the wearer to benefit from an optical power correction that is adapted to various vision distances without changing spectacles. They may also correct other visual defects, such as astigmatism for example.

A progressive ophthalmic lens has a variable power over the surface of the lens.

For example provision is made for a first vision zone for far vision having a first average power value, a second vision zone for near vision having a second average power value and, between these two zones, a third vision zone for intermediate vision, the curvature of which varies gradually and which is called the progression corridor.

The fitting height of the ophthalmic lens corresponds to the height, relative to the lower edge of the rim of the frame, of the projection of the pupil of the wearer having a predetermined primary gaze direction onto a mean plane of this rim of the chosen frame, corresponding to a mean surface or mean plane of the ophthalmic lens once fitted into said frame.

This predetermined primary gaze direction corresponds to the gaze direction of the wearer under far-vision conditions.

Thus, the positions of the near- and far-vision zones of the wearer are parameters that are very important for the personalized design of progressive ophthalmic lenses. These near- and far-vision zones of the wearer constitute two zones of use of the ophthalmic lens.

Devices for tracking wearer gaze direction belonging to measuring-totem or measuring-tablet type families of optical measuring devices are known.

However, these devices for tracking gaze direction have the drawback of not allowing this gaze direction to be tracked under natural, i.e. unconstrained, wearer visual behavior and posture conditions since the wearer must stand up or sit down in front of the measuring totem or hold the measuring tablet in his hands.

SUBJECT OF THE INVENTION

In order to remedy the aforementioned drawback of the prior art, the present invention proposes a device for determining the position of a noteworthy point of an eye of the wearer under natural wearer visual behavior and posture conditions, which may be used in a device for tracking wearer gaze direction able to allow this tracking to be carried out under natural wearer visual behavior and posture conditions.

More particularly, according to the invention a device is provided for determining the position of a noteworthy point of an eye of a wearer equipped with a vision frame, comprising at least one image-capturing apparatus, and positioning means for positioning the image-capturing apparatus with respect to said vision frame, in such a way that, when said vision frame is placed in useful position on the head of the wearer, the image-capturing apparatus is suitable for capturing an image of this eye of the wearer, and means for determining the position of a noteworthy point of the eye of the wearer from said at least one image of the eye of the wearer which was captured by the image-capturing apparatus.

Thus, the device for determining the position of a noteworthy point of the eye of the wearer according to the invention is suitable for allowing this position to be determined under posture and visual behavior conditions that are natural for this wearer, i.e. unconstraining.

In particular, the device for determining the position of the noteworthy point of the eye may be at least partially mounted on the vision frame of the individual in question.

This vision frame is preferably either the usual pair of spectacles of the individual, said pair of spectacles being equipped with its corrective ophthalmic lenses. It may also be a question of a pair of spectacles newly chosen by this individual, said pair of spectacles optionally being equipped with optionally corrective ophthalmic lenses.

The vision frame may also comprise an optionally full-rimmed spectacle frame. Said frame may be of the half-rimmed, nylon-wire type or of the rimless, drilled type. It may also be a question of a pair of goggles or a virtual reality headset. It includes one or two frame temples and may be equipped with one or two ophthalmic lenses or one or two displaying devices.

The determination of the position of the noteworthy point of the eye allows the gaze direction during various tasks of the individual to be determined.

Furthermore, the device for determining the position of a noteworthy point may be used to measure other quantities such as the height of the eyes of the wearer with respect to the lower edge of the lens or of the spectacle frame, the interpupillary distance, the position of the eye rotation centers, the distance between the back face of the ophthalmic lens and the top of the cornea of the eye.

The values of these quantities in their turn allow the geometrico-postural parameters required for the optical design of the ophthalmic lenses intended for the wearer and for the chosen frame to be determined.

The following are other nonlimiting and advantageous features of the device according to the invention:

provision is furthermore made for at least one light source arranged so as to illuminate at least one eye of the wearer, the image captured by the image-capturing apparatus then comprising an image of at least this eye of the wearer illuminated by said light source;

said positioning means are suitable for positioning said device with respect to said vision frame in such a way that, when said vision frame is placed in useful position on the head of the wearer, the light source is suitable for illuminating the eye of the wearer;

the vision frame comprising at least one frame temple for its installation on the head of the wearer, the positioning means are suitable for interacting with the vision frame of the wearer, such that each light source and each image-capturing apparatus is placed on the side of the vision frame on which said frame temple extends;

said vision frame including at least one rim and/or one ophthalmic lens, each light source and each image-capturing apparatus is arranged such that it is placed facing said rim or said ophthalmic lens of the vision frame when the positioning means are interacting with said vision frame;

said vision frame including at least two rims and/or two ophthalmic lenses, provision is made for at least two light sources and two image-capturing apparatuses, which are arranged such that at least one of the two light sources and one of the two image-capturing apparatuses is placed facing each rim or each ophthalmic lens of the vision frame when the positioning means are interacting with said vision frame;

provision is made for four image-capturing apparatuses that are arranged such that two image-capturing apparatuses are placed facing each rim or each ophthalmic lens of the vision frame when the positioning means are interacting with the vision frame;

said positioning means are positioning means that make the device removable while permitting the device to be mounted on the vision frame and this device to be demounted;

said vision frame including at least two rims and/or two ophthalmic lenses, said positioning means comprise a measuring support that is equipped with a horizontal bar and two lateral arms, and two clips belonging to said horizontal bar and suitable for interacting with an upper portion of the rims or ophthalmic lenses of the vision frame, and two clips that are each placed at the end of one of the lateral arms and suitable for interacting with a lower portion of the rims or of the lenses of the vision frame;

each light source and each image-capturing apparatus is borne by one of the lateral arms of the measuring support;

said measuring support furthermore comprises a supporting ring that is mounted on said horizontal bar and supports said at least one light source and said at least one image-capturing apparatus.

said supporting ring is mounted on said horizontal bar so as to be translationally movable along an axis parallel to the straight line joining the two clips of the horizontal bar and/or translationally movable along an axis perpendicular to this straight line;

said supporting ring is open or closed;

said measuring support furthermore includes at least one waveguide guiding the light emitted by said light source;

each light source is a light-emitting diode emitting in the domain of the infrared wavelengths.

The invention also relates to a device for tracking the gaze direction of a wearer equipped with a vision frame, comprising a device for determining the position of a noteworthy point of an eye of the wearer such as described above, and means for determining the gaze direction of the wearer depending on the position of this noteworthy point of the eye.

Thus, the device for tracking the direction of the gaze according to the invention is suitable for allowing this gaze direction to be determined under posture and visual behavior conditions that are natural for the individual, i.e. unconstraining.

In particular, the device for tracking the direction of the gaze may be at least partially mounted on the vision frame of this individual. This vision frame is preferably either the usual pair of spectacles of the individual, said pair of spectacles being equipped with its corrective ophthalmic lenses. It may also be a question of a pair of spectacles newly chosen by this individual, said pair of spectacles optionally being equipped with optionally corrective ophthalmic lenses.

The vision frame may also comprise an optionally full-rimmed spectacle frame. Said frame may be of the half-rimmed, nylon-wire type or of the rimless, drilled type. It may also be a question of a pair of goggles or a virtual reality headset. It may also be a trial frame (ISO 12867:1998). It includes one or two frame temples and may be equipped with one or two ophthalmic lenses or one or two displaying devices.

Tracking gaze directions during various tasks of the individual for example allows the zones of use of the ophthalmic lenses intended to equip the pair of spectacles of the individual, and in particular the far- and near-vision zones of the individual, to be determined with precision.

The zones of use correspond to those zones of the ophthalmic lens in which the points of intersection of the gaze direction of the wearer and of the ophthalmic lens are found when the wearer scans his gaze over a portion of his environment.

Furthermore, the device for tracking the direction of the gaze may be used to measure other quantities such as the height of the eyes of the wearer with respect to the lower edge of the lens or of the spectacle frame, the interpupillary distance, the position of the eye rotation centers, the distance between the back face of the ophthalmic lens and the top of the cornea of the eye.

The values of these quantities in their turn allow the geometrico-postural parameters required for the optical design of the ophthalmic lenses intended for the wearer and for the chosen frame to be determined.

The invention also provides a method for determining the position of a noteworthy point of at least one eye of a wearer equipped with a vision frame, by means of a device for determining the position of this noteworthy point such as described above, including at least one image-capturing apparatus that is arranged to be facing this eye of the individual, comprising the following steps:

a) positioning the device for determining the position of a noteworthy point of the eye of the wearer with respect to the vision frame of the wearer, c) capturing at least one image of the eye of the wearer with the image-capturing apparatus of said tracking device, d) determining the position of the noteworthy point of the eye from the captured image.

Thus, the method according to the invention permits the position of the noteworthy point of the eye of the wearer to be determined under the usual visual behavior and posture conditions of the individual.

It is then possible to deduce therefrom the gaze directions of the wearer during various tasks of the individual thereby allowing the position and extent of the far- and near-vision zones of the individual on the corresponding ophthalmic lens intended for the wearer and for the frame chosen thereby to be deduced with precision.

The following are other nonlimiting and advantageous features of this method according to the invention:

- in step a), the device for determining the position of a noteworthy point of the eye of the wearer is positioned with respect to the vision frame of the wearer such that said at least one image-capturing apparatus is suitable for capturing an image of the eye of the wearer;
- the device for determining the position of a noteworthy point of the eye of the wearer including at least two image-capturing apparatuses that are arranged so as to be facing the eye of the wearer, in step d), the position of the noteworthy point of the eye is determined via a triangulation calculation from two images that are captured by the two image-capturing devices.

The invention also relates to a method for determining the gaze direction of at least one eye of a wearer equipped with a vision frame, by means of a device for tracking gaze direction such as described above, including at least one image-capturing apparatus that is arranged to be facing this eye of the wearer, comprising the following steps:

e) a step of determining the position of a noteworthy point of at least one eye of the wearer using the determining method such as described above, f) a step of determining the gaze direction of the wearer depending on the position of this noteworthy point of the eye.

Thus, the method according to the invention permits the gaze direction of the wearer to be determined under the usual visual behavior and posture conditions of the individual.

Determining the gaze directions of the individual during various tasks allows the position and extent of the far- and near-vision zones of the individual on the corresponding ophthalmic lens intended for the wearer and for the frame chosen thereby to be deduced with precision.

The following are other nonlimiting and advantageous features of this method according to the invention:

- in step e), the gaze direction is determined by calculation, on the basis of a predetermined model of the eye;
- the noteworthy point of the eye the position of which is determined in step d) being the center of the pupil of the eye or a point on the outline of the pupil of the eye, in step e), the position of a rotation center of the eye or of a center of the curvature of the cornea of the eye is determined and the gaze direction is deduced therefrom as being the straight line joining this rotation center of the eye or this center of the curvature of the cornea and the center of the pupil or a point on the outline of the pupil.
- the device for tracking gaze direction includes at least three light sources that are facing the eye of the wearer and,
- in step d):
- the corneal reflections of the three light sources and the image of the noteworthy point of the eye are identified in the image captured in step c)
- the relative position of the noteworthy point and of the corneal reflections is determined,
- and in step e):
- the direction of the gaze of the wearer in a predetermined frame of reference is deduced from the position of the light sources in this predetermined frame of reference from the relative position of the noteworthy point and of the corneal reflections.

Lastly, the invention relates to a method for determining a zone of use of an ophthalmic lens by a wearer of a vision frame comprising at least one frame and/or one ophthalmic lens, wherein

- a plurality of directions of the gaze of this wearer are determined using the method for determining the direction of the gaze such as described above,
- for each direction of the gaze, its point of intersection with a predetermined surface relating to the frame and/or to the ophthalmic lens of the wearer is determined,
- said zone of use is determined depending on said points of intersection.

DETAILED DESCRIPTION OF AN EXEMPLARY EMBODIMENT

The description which follows with reference to the appended drawings, which are given by way of nonlimiting examples, will make it easy to understand the essence of the invention and how it can be achieved.

In the appended drawings:

FIG. 1 is a schematic front view of a pair of spectacles equipped with a first embodiment of the device for tracking gaze according to the invention, FIG. 2 is a schematic front view of a pair of spectacles equipped with a second embodiment of the device for tracking gaze according to the invention, FIG. 3 is a schematic rear perspective view of a pair of spectacles equipped with a third embodiment of the device for tracking gaze according to the invention, FIG. 4 is a partial schematic view of the device for tracking gaze in FIG. 2, FIGS. 5 to 7 illustrate various implementations of the method for tracking gaze directions according to the invention.

DEVICE

In FIGS. 1 to 3, a plurality of embodiments of the device 100; 200; 300 for tracking gaze direction according to the invention have been shown.

As explained below, each of these embodiments corresponds to one embodiment of the device for determining the position of a noteworthy point of the eye of the wearer.

The wearer is any individual equipped with a vision frame.

This device 110; 200; 300 for tracking gaze direction is suitable for being fastened to the vision frame of the wearer. It is here a question of a pair of spectacles 400 of the wearer.

This pair of spectacles 400 here includes, as in particular shown in FIGS. 1 to 3, a spectacle frame 410 chosen by the wearer and two ophthalmic lenses 420.

It may be a question of the pair of spectacles chosen by the wearer for their appearance and not including corrective ophthalmic lenses, of the usual pair of spectacles of the wearer already including corrective ophthalmic lenses adapted to his vision, or of a trial frame including corrective ophthalmic lenses adapted to the vision of the wearer.

In the illustrated example, the spectacle frame 410 is of full-rimmed type, i.e. the frame 410 includes rims 411, 412 in which the ophthalmic lenses are mounted.

These two rims 411, 412 are rigidly connected by a nose bridge 413. This nose bridge 413 includes two surfaces that rest on the sides of the nose of the wearer.

Each rim 411, 412 is also connected to a frame temple 414, 415 conventionally hinged to the corresponding rim.

Below, the frame temples will be considered to be fixed in their open position with respect to one another, i.e. in the position suitable for the placement of the pair of spectacles in useful position on the head of the wearer.

In this useful position, which is the position of wear of the pair of spectacles 400, the frame temples 414, 415 of the frame 410 each rest on one of the ears of the wearer and the nose bridge 413 of the frame 410 rests on the nose of the wearer.

Each rim 411, 412 of the frame 410 is then placed facing one of the eyes of the wearer, so that the corresponding ophthalmic lens is itself placed facing one eye of the wearer.

The wearer looks through these ophthalmic lenses.

The frame 410 shown in the examples in the figures is here a frame made of plastic. Therefore, the nose bridge 413 includes two surfaces that rest on the sides of the nose of the wearer that here are fixed. As a variant, the frame may be a metal frame. The surfaces that rest on the nose of the wearer are then borne by two pads each of which is connected to the nose bridge by an arm. The relative position of these pads is then adjustable.

As a variant, the vision frame may also comprise a non-full-rimmed spectacle frame. Said frame may be of the half-rimmed, nylon-wire type or of the rimless, drilled type.

In the latter case, the ophthalmic lenses are drilled with through-holes and each maintained by one end of the nose bridge and one end of that frame temple which is associated with the ophthalmic lens, which interact with the through-holes in the lenses. This type of frame is similar to that described above, except that it does not include rims. The nose bridge and the frame temples are similar.

The vision frame may also consist of goggles or an augmented reality headset or a trial frame. It includes one or two frame temples and may be equipped with one or two ophthalmic lenses or one or two displaying devices.

The device 100; 200; 300 for tracking gaze direction comprises, generally, a device for determining the position of a noteworthy point of an eye of the wearer and means for determining the gaze direction of the wearer depending on the position of this noteworthy point of the eye.

More precisely, the device for determining the position of a noteworthy point of an eye of the wearer comprises at least one image-capturing apparatus 120; 220; 320.

It furthermore comprises positioning means for positioning the image-capturing apparatus 120; 220; 320 with respect to said pair of spectacles, in such a way that, when said pair of spectacles 400 is placed in useful position on the head of the wearer, the image-capturing apparatus 120; 220; 320 is suitable for capturing an image of this eye of the wearer.

The device for determining the position of a noteworthy point of the eye of the wearer lastly comprises means for determining this position from said at least one image of the eye of the wearer which was captured by the image-capturing apparatus.

Preferably, as is the case in the examples of the figures, the device for determining the position of a noteworthy point of the eye also comprises at least one light source 110; 210; 310.

The positioning means are then suitable for positioning the light source 110; 210; 310 with respect to said pair of spectacles, in such a way that, when said pair of spectacles 400 is placed in useful position on the head of the wearer, said at least one light source 110; 210; 310 is suitable for illuminating at least one eye of the wearer.

The device for determining the position of a noteworthy point of the eye of the wearer is distinct from the vision frame of the wearer. It is a question of a removable device, in the sense that the means for positioning this device on the vision frame permit the device to be mounted on the vision frame, so as to fasten the device to the vision frame, and this device to be demounted, so as to disassociate the device from the vision frame.

The image-capturing apparatus 120; 220; 320 is then suitable for capturing an image of this eye of the wearer illuminated by said light source 110; 210; 310.

The means for determining the position of the noteworthy point of the eye are then programmed to determine this position from said at least one image of the eye of the wearer i.e. the image captured by the image-capturing apparatus when this eye is illuminated by the light source 110; 210; 310.

The means for determining the gaze direction of the wearer are suitable for determining the gaze direction of the wearer depending on the position of the noteworthy point, and therefore from said at least one image of the eye of the wearer i.e. the image captured by the image-capturing apparatus when this eye is illuminated by the light source 110; 210; 310.

More precisely, in the examples shown in FIGS. 1 to 4 and described here, the positioning means are suitable for interacting with the pair of spectacles 400 of the wearer in order to position each light source 110; 210; 310 and each image-capturing apparatus 120; 220; 320.

In practice, these positioning means here include a measuring support 150; 250; 350 equipped (FIGS. 1 to 3) with a main bar 151; 251; 351 that is suitable for being placed above the pair of spectacles 400 and two lateral arms 152; 252; 352, and means 130; 230; 330 for mounting this measuring support 150; 250; 350 on the pair of spectacles.

The main bar 151; 251; 351 takes the form of a straight and rigid rod. It is intended to extend substantially in a mean plane of the ophthalmic lenses 420 mounted in the frame 410, which corresponds to the mean plane of the rims 411, 412 of the frame 410 in the case of the full-rimmed frame shown in the figures.

As a variant, this main bar may take the form of a curved rod or a rod including two hinged portions intended to be placed in correspondence with each rim of the frame or with each ophthalmic lens of the pair of spectacles.

This main bar 151; 251; 351 has a length slightly larger than the usual overall width of a spectacle frame. This overall width generally corresponds to the width measured between the external faces of the frame temples 414, 415 of the frame 410.

The lateral arms 152; 252; 352 each extend from a free end of the main bar 151; 251; 351, on the same side of this main bar 151; 251; 351.

In this way, the lateral arms 152; 252; 352 are suitable for partially encircling the rims 411, 412 of the frame 410 or the ophthalmic lenses 420.

Each lateral arm 152; 252; 352 takes the form of a leaf spring fastened at one of its ends to the main bar 151; 251; 351. A portion of the means 130; 230; 330 for mounting the measuring support 150; 250; 350 is placed on the main bar 151; 251; 351 and another portion is placed at the free end of each lateral arm 132; 232; 332.

More precisely, these mounting means 130; 230; 330 on the one hand comprise two upper clips 131, 132; 231, 232; 331, 332 that extend from the main bar 151; 251; 351 and, on the other hand, two lower clips 133, 134; 233, 234; 433, 434 that each extend from the free end of one of the lateral arms 152; 252; 352.

Each clip 131, 132, 133, 134; 231, 232, 233, 234; 331, 332, 433, 434 here comprises two small cones made of flexible plastic each forming a pincer suitable for being attached to the rims 411, 412 of the frame 410 or to the ophthalmic lenses if the frame is of the drilled type. In practice, a portion of the frame or of the lens is inserted between the two small cones, which deform to allow this insertion. They then exert a sufficient pressure on the frame or the ophthalmic lenses to maintain the measuring support 150; 250; 350 in place on the pair of spectacles.

Whatever the embodiment envisioned here, the means 130; 230; 330 for mounting the measuring support 150; 250; 350 are suitable for mounting said measuring support on the pair of spectacles 400 of the wearer, such that each light source 110; 210; 310 and each image-capturing apparatus 120; 220; 320 of the measuring support 150; 250; 350 is placed between the frame temples 414; 415 of the pair of spectacles 400.

In other words, the mounting means 130; 230; 330, the light sources 110; 210; 310 and the image-capturing apparatuses 120; 220; 320 are arranged so as to extend between the eyes of the wearer and the rims 411, 412 of the frame 410, or the ophthalmic lenses when the frame is of the drilled type, when the measuring support 150; 250; 350 is mounted on the pair of spectacles 400 and the pair of spectacles 400 is placed on the face of the wearer.

Thus, generally, if the vision frame were to comprise only a single frame temple for its installation on the head of the wearer, the positioning means would then be suitable for interacting with this vision frame in such a way that each light source and each image-capturing apparatus would be placed on the side of the vision frame on which said frame temple extends.

As a variant, it may be envisioned that the mounting means of the measuring support be suitable for mounting said measuring support on the vision frame of the wearer, such that each light source and/or each image-capturing apparatus of the measuring support is placed on that side of the rims or of the ophthalmic lenses which is opposite each frame temple of the vision frame.

In this case, the light sources and/or the image-capturing apparatuses are placed on the exterior of the vision frame, such that the rims of the frame and/or the ophthalmic lenses are located between the eyes of the wearer and the light sources and image-capturing apparatuses of the device for tracking gaze directions when the vision frame is placed on the face of the wearer.

Whatever the envisioned embodiment, the light sources 110; 210; 310 are advantageously light sources that emit at infrared wavelengths. The emitted light is then not visible by the wearer, and does not perturb his posture and visual behavior. In contrast, this infrared light may be detected by the sensor of the corresponding image-capturing apparatuses.

These image-capturing apparatuses are preferably video cameras that are suitable for detecting light emitted at infrared wavelengths.

Advantageously, the measuring support 150; 250; 350 also includes a projection 155; 255; 355 that extends perpendicularly to the main bar 151; 251; 351, in a plane substantially perpendicular to the mean plane of the rims 411, 412 of the frame 410, or of the ophthalmic lenses in the case of a drilled frame, when the measuring support 150; 250; 350 is fastened to this frame 410, and a protruding element 156; 256; 356 that rises up perpendicularly to the main bar 151; 251; 351 and to the projection 155; 255; 355, in the mean plane of the rims 411, 412 of the frame 410 or in a plane parallel to this mean plane, when the measuring support 150; 250; 350 is fastened to this frame 410.

Here, the measuring support 150, 250, 350 furthermore includes three or four locating elements R1, R2. These locating elements are not the subject of the invention and only a few of their features will be recalled here.

One or two first locating elements R1, R2 are placed at one of the ends of the main bar 151 or at each of these ends, and are oriented so as to be visible in a front-on image of the wearer, when the measuring support 150; 250; 350 is fastened to the frame 410 of the wearer.

A second locating element R1, R2 is placed on the protruding element 156; 256 and a third locating element R1, R2 is placed at the end of the projection 155; 255, such that these two locating elements are visible in a front-on image of the wearer.

Furthermore, the second and third locating elements R1, R2 are placed such that, in a front-on image of the measuring support 150; 250; 350, they are located one below the other.

The locating elements of the third embodiment of the measuring support 350 are not shown in FIG. 3.

Each locating element R1, R2 has one or more predetermined geometrical characteristics, for example its dimensions or the dimensions of a geometric pattern borne thereby. The geometric pattern may for example take the form of a reticle or of alternate contrasted bands.

Generally, various configurations may be envisioned as regards the number and positions of the light sources and image-capturing apparatuses.

Provision may for example be made for at least two light sources and two image-capturing apparatuses, which are arranged such that at least one of the two light sources and one of the two image-capturing apparatuses are placed facing each rim or each ophthalmic lens of the pair of spectacles when the mounting means of the measuring support are interacting with said pair of spectacles.

This is the case in the first and second embodiments of the device 100; 200 for tracking gaze direction shown in FIGS. 1 and 2.

Then, at least one light source and one image-capturing apparatus is placed in correspondence with each eye of the wearer.

This advantageously allows data to be acquired for both eyes of the wearer simultaneously. Bulk is decreased and the obstruction of the field of vision of the wearer associated with the presence of these elements is limited.

Preferably, a light source that is not very directional, i.e. one that is suitable for illuminating the largest possible portion of the eye of the wearer, and a wide-angle image-capturing apparatus, i.e. one with a small focal length, are used.

However, provision is preferably made, for each eye of the wearer, for at least one light source, allowing at least this eye of the wearer to be illuminated, and for at least two image-capturing apparatuses allowing stereoscopic images of this eye of the wearer to be recorded.

Furthermore, provision is preferably made for two light sources that are in correspondence with each eye of the wearer, thereby permitting the corneal reflections of these two light sources to be sought in the recorded images, as explained below.

More precisely, in the first embodiment of the device for tracking gaze direction shown in FIG. 1, provision has been made for two light sources 110 and two video cameras 210, which are placed in proximity to each rim 411, 412 of the frame 410.

Each light source 110 and each image-capturing apparatus 210 is borne by one of the lateral arms 152 of the measuring support 150.

Each light source 110 is here associated with a video camera 210 in a measuring element 130A, 130B, 130C, 130D.

Each measuring element 130A, 130B, 130C, 130D thus comprises a casing housing one of the light sources 110 and one of the video cameras 210.

Each measuring element 130A, 130B, 130C, 130D also comprises means for attaching the casing to one of the lateral arms 152 of the measuring support 150.

These attaching means may for example include a housing through which the corresponding lateral arm 152 of the measuring support 150 passes and a screw that is tightened against this lateral arm 152.

It may also be a question of any other type of attaching means, for example screw-fastening, adhesive-bonding, clip-fastening, or interfitting attaching means.

As FIG. 1 shows, the measuring elements 130A, 130B, 130C, 130D are distributed so that the field of the two video cameras 210 placed in proximity to each eye of the wearer covers the largest possible portion of the eye of the wearer, and preferably at least one portion comprising the pupil of this eye.

In practice, on each lateral arm 152 of the measuring support 150, one 130B, 130C of the measuring elements is placed in proximity to the end of this lateral arm 152 including the means 133, 134 for mounting the measuring support 150 on the pair of spectacles 400 of the wearer and the other 130A, 130D of the measuring elements is placed approximately in the middle of the lateral arm 152.

Such a measuring support has the advantage of being easily adaptable to any type of spectacle frame: rims made of plastic, rims made of metal, drilled, half-rimmed, etc. whatever the size of the frame.

Furthermore, the placement of the measuring elements does not greatly hinder the vision of the wearer. The field of vision of the latter is not particularly perturbed.

This measuring support 150 is preferably made from a material that is not very dense so as to not excessively increase the weight of the pair of spectacles of the wearer.

In the second embodiment of the device 200 for tracking gaze direction shown in FIG. 2, provision has been made, by way of illustration, for a configuration in which the light sources and video cameras are different for each eye of the wearer.

Specifically, the measuring support 250 here comprises, on the one hand two video cameras 220 and six light sources 210, which are suitable for being placed facing the right eye of the wearer, and on the other hand, two video cameras 220 and two light sources 210, which are suitable for being placed facing the left eye of the wearer.

More precisely, the measuring support 250 here comprises two supporting rings 253, 254 that are mounted on said horizontal bar 151 of the measuring support 150.

A first supporting ring 253 is suitable for being placed facing the right eye of the wearer, and the second supporting ring 254 is suitable for being placed facing the left eye of the wearer.

Each supporting ring 253, 254 supports all the video cameras 220 and light sources 210 that are suitable for being placed facing the corresponding eye.

Each supporting ring 253, 254 is fastened to a vertical pole 255, 256 that is mounted on a secondary bar 257.

The secondary bar 257 extends parallelly to the main bar 251 of the measuring support 250. It is mounted on another portion of the measuring support 250, here on the projection 255 of the measuring support 250.

Furthermore, preferably, the vertical poles 255, 256 are each mounted so as to be translationally movable on the secondary bar 257, along the latter and perpendicularly to the latter. This may for example be achieved by virtue of a sliding connection and a rack. The vertical poles are then independently translationally movable between the eyes of the wearer.

The vertical poles 255, 256 are translationally movable along an axis parallel to the straight line joining the two clips 231, 232 of the horizontal bar 251 and/or translationally movable along an axis perpendicular to this straight line.

Here, the straight line joining the two clips 231, 232 of the horizontal bar 251 is parallel to the main bar 251 of the measuring support 250.

The vertical poles 255, 256 are here translationally movable parallelly to this main bar 251 and perpendicularly thereto, in a plane substantially perpendicular to the projection 255. Thus, in the position in which the measuring support is used, the supporting rings 253, 254 are translationally movable in two orthogonal directions in a plane substantially parallel to the mean plane of the rims of the frame or of the ophthalmic lenses.

These two degrees of freedom permit each supporting ring 255, 256 to be precisely positioned in front of the eye of the wearer, and even each supporting ring to be centered on the pupil P of the corresponding eye of the wearer, as schematically shown in FIG. 2.

As a variant, the secondary bar may be mounted so as to be translationally movable parallelly to the main bar of the measuring support. This may for example be achieved using a slide provided in the projection and in which the secondary bar slides.

It may also be envisioned that the supporting rings be translationally movable in a third direction orthogonal to the two first mobility directions described above. This then allows the distance between the supporting rings and the eyes of the wearer to be modified.

Furthermore, it is also possible to envision rotational mobilities about the vertical poles and about two axes that are perpendicular to each other and perpendicular to the corresponding vertical pole. Mobilities including translational movements and/or pivoting movements in combination may also be envisioned.

As a variant, it may also be envisioned that the supporting rings remain fixed i.e. not movable with respect to the main bar of the measuring support.

In the case where the light sources and the image-capturing apparatuses are placed on the exterior of the pair of spectacles, such rotational mobilities allow prismatic effects introduced by the presence of the ophthalmic lens between the eye of the wearer and the image-capturing apparatuses and light sources of the device for tracking gaze direction to be taken into account.

The first supporting ring 253 is a closed ring, whereas the second supporting ring 254 is an open ring.

Use of the closed first supporting ring 253 has the advantage of allowing a larger number of video cameras and light sources to be arranged on this ring. Use of the open second supporting ring 254 has the advantage of limiting the extent of the field of vision of the wearer obstructed by the measuring support.

Generally, each supporting ring 253, 254 is furthermore preferably made from a transparent material and has the smallest possible radial and axial thickness. Furthermore, the diameter of the supporting ring 253, 254 is chosen so as to preserve the field of vision of the wearer.

The inside diameter of the supporting ring is for example comprised between 2 and 4 centimeters.

Each supporting ring 253, 254 may furthermore include one or more position markers 240 (not shown in FIG. 2, but visible in FIG. 4) permitting a predetermined adjustment of the position of the image-capturing apparatuses and of the light sources with respect to the eyes and in particular pupils P of the wearer. Thus, the relative position of each light source 210 and each image-capturing apparatus 220 being known and set with respect to the position marker on the supporting ring 253, 254, the position of these position markers 240 with respect to the pupil P of the wearer allows the light sources 210 and the image-capturing apparatuses 220 be placed in a known and predetermined position with respect to the pupil P of the wearer.

This position adjustment will be described below.

Here, as mentioned above, six light sources and two video cameras are supported by the first supporting ring 253, whereas two light sources and two video cameras are supported by the second supporting ring 254.

These light sources and video cameras are fastened to the corresponding supporting ring by any means known to those skilled in the art, for example by screwing, adhesive bonding, clip fastening, interfitting.

As FIG. 2 shows, the light sources 210 and the video cameras 220 are distributed around each supporting ring 253, 254 so that the field of the two video cameras 220 placed in proximity to each eye of the wearer covers the largest possible portion of the eye of the wearer, and preferably at least one portion comprising the pupil of this eye, so as to be able to follow the position of the pupil of the eye in the largest possible number of gaze directions.

On the two supporting rings 253, 254, the two video cameras are separated by an angle at the center of about 120 degrees, and are symmetric with respect to a plane passing through a diameter of the supporting ring and perpendicular to the straight line joining the mounting clips 231, 232 of the main bar 251 of the measuring support 250.

The light sources 210 are regularly distributed in diametrically opposite pairs.

This measuring support 250 has the advantage of guaranteeing the light sources and video cameras are precisely positioned independently of the shape of the frames chosen by the wearer.

As is the case of the third embodiment in FIG. 3, provision may also be made for the light sources 310 and the image-capturing apparatuses 320 of the measuring support 350 to be arranged such that they are placed facing a single rim 412 or a single ophthalmic lens of the pair of spectacles 400 when the mounting means 330 of the measuring support 350 are interacting with said pair of spectacles.

More precisely, the measuring support 350 of the third embodiment here includes a single supporting ring 353 supporting six light sources 310 and two video cameras 320.

Generally, it is possible to envision at least one light source and at least one image-capturing apparatus that are suitable for being placed facing a given rim of the frame or a given ophthalmic lens of the pair of spectacles.

The supporting ring 353 is almost identical to the first supporting ring 253 of the second embodiment described above and will not be described in more detail here.

The supporting ring 353 is here fastened to the main bar 351 of the measuring support 350, level with one of the clips 332 for fastening the main bar 351 to the pair of spectacles 400. It is here fastened without mobility to a rigid tongue that extends from the main bar 351.

The tracking of gaze direction is here monocular.

Whatever the embodiment in question, the device for tracking the direction of the gaze obtained is a miniature, autonomous and portable device.

The image-capturing apparatuses 120; 220; 320 of the measuring support communicate with the means for determining the position of the noteworthy point of the eye of the wearer, and therefore with the means for determining the gaze direction of the wearer, in order to transmit thereto the recorded images.

The means for determining the position of the noteworthy point of the eye of the wearer, and therefore the means for determining the gaze direction of the wearer, may also communicate with the light sources, for example so as to control their turn-on/turn-off.

For this purpose, the measuring support comprises a communications interface for communications between the light sources and/or the image-capturing apparatuses and the means for determining the position of the noteworthy point of the eye of the wearer and/or gaze direction. It is a question of any communications interface known to those skilled in the art. This communications interface may be a wired or wireless interface.

It exchanges data with a remote post, in particular for an initialization phase and a final phase of recuperating recorded data. These phases will be described below.

In practice, the means for determining the position of the noteworthy point of the eye of the wearer and the means for determining the direction of the gaze generally comprise remote computational means programmed to implement one of the embodiments of the method for determining the position of the noteworthy point of the eye of the wearer and the gaze direction according to the invention described below, respectively. These determining means are here grouped together in a single computational terminal.

Optionally, the device for determining the position of a noteworthy point of the eye of the wearer, and therefore the device for tracking gaze direction, may also comprise other elements making it multifunctional.

It may in particular include one or more scene video cameras, i.e. video cameras that are turned away from the wearer so as to capture images of his environment. This is in particular useful for the classification of the activities of the wearer, for the enrichment of the map of distance disparities, and for the evaluation of the luminosity map of the environment of the wearer. The visual behavior of the wearer may thus be placed in relationship with the various activities of the wearer. The eye-head behavior, the postures and movements of the wearer are thus more precisely determined.

It may also include additional sensors, in particular miniature sensors such as accelerometers, gyroscopes, magnetometers, luminosity sensors, distance and proximity sensors, global positioning sensors.

It may lastly comprise means allowing the wearer and the device 100; 200; 300 for tracking gaze direction to interact, in particular via buttons and other haptic sensors, and devices for feeding back information such as light-emitting diodes, miniature screens, a head-up display, vibrators, voice synthesis, etc.

As a variant, it is possible to envision the positioning means being suitable for interacting with the pair of spectacles of the individual in order to position only each image-capturing apparatus. Said means then possibly possess additional means for positioning the one or more light sources.

In such a variant, the light sources of the device for tracking gaze direction may be remote.

In other words, the light sources may be positioned elsewhere than on the pair of spectacles of the wearer, at a distance from said pair of spectacles. It is for example possible to envision the light sources being fastened to a wall facing the wearer, by virtue of various fastening systems provided in the wall. The wearer is for example positioned in a given location marked by a mark on the ground. The mark on the ground and the systems for fastening the light sources to the wall are arranged so that each light source illuminates at least one of the eyes of the wearer. They then form part of the positioning means of the device for tracking the direction of the gaze.

Lastly, it is also possible to envision that the role of these light sources be played by ambient light, whether this be sunlight or artificial ambient light. The one or more light sources may in this case not be included in the device for determining the position of a noteworthy point of the eye and therefore in the device for tracking gaze direction.

According to another variant of the device according to the invention, it is possible to envision that the measuring support furthermore includes at least one waveguide guiding the light emitted by a light source.

Thus, it is possible to envision the light sources being located outside of the field of vision of the wearer, their light being guided as far as the eye of the wearer by such a waveguide.

Advantageously, it is possible to envision the supporting ring of the second and third embodiments itself forming a waveguide. The light source associated with this waveguide may be positioned away from the head of the wearer or indeed be placed on the measuring support, on the main bar or on one of the lateral arms.

As a variant, the waveguide may also be placed on that side of the vision frame which is opposite that on which the one or more frame temples of this frame extend.

The waveguide may in particular be placed in proximity to the front face of the ophthalmic lenses of the vision frame.

The waveguide may also comprise one or more optical fibers. Such a variant has the advantage of limiting the obstruction of the field of vision of the wearer.

Many variants may be envisioned for the device described above.

It is for example possible to envision a measuring support including at least one supporting ring that is similar to that described above, but equipped with mounting means that are suitable for mounting this ring directly on the pair of spectacles, for example by means of a sucker permitting the supporting ring to be attached to an ophthalmic lens of the pair of spectacles.

It is also possible to envision that the supporting ring be replaced by a filamentary structure having any shape suitable for preserving the field of vision of the wearer, made for example of a preferably transparent wire, which may be flexible or not.

It is also possible to envision that the measuring support comprise a planar lens having a shape close to that of the rims of the frame, on which lens are mounted a supporting ring and/or the image-capturing apparatuses and/or the light sources, the plano afocal lens possibly being fastened to the frame by any means known to those skilled in the art, for example by a fastening system including clips and/or magnets.

Method

The device 100; 200; 300 for tracking the direction of the gaze described above is used in the personalized optical design of ophthalmic lenses that are adapted both to the wearer and to the chosen frame.

In particular, it is used to determine the position and extent of the zones of use of each ophthalmic lens intended for the wearer and for the chosen frame. To do this, the gaze directions of the wearer, then the points of intersection of these gaze directions of the wearer with a plane associated with the frame or with the ophthalmic lens in question, are determined as the wearer carries out various visual tasks while he is equipped with the device for tracking gaze direction described above.

Generally, to determine the gaze direction of at least one eye O1 of the wearer equipped with the pair of spectacles 400, by means of the device 100; 200; 300 for tracking gaze direction, which includes at least one light source 110; 210; 310 and at least one image-capturing device 210; 220; 320, the operator carries out the following steps:

a) a step of positioning the device 100; 200; 300 for tracking gaze direction comprising the device for determining a noteworthy point of the eye with respect to the pair of spectacles 400 of the wearer, c) a step of capturing at least one image of the eye of the wearer with the image-capturing apparatus 120; 220; 320 of said tracking device 100; 200; 300, d) a step of determining the position of a noteworthy point of the eye from the captured image, e) a step of determining the gaze direction of the individual depending on the position of this noteworthy point of the eye.

Preferably, the tracking device 100; 200; 300 comprises at least one light source 110; 210; 310.

The method for determining gaze direction then furthermore comprises a step b) of illuminating the eye O1 of the wearer by virtue of the light source 110; 210; 310 of said tracking device 100; 200; 300.

The steps a), b), c), d) constitute a method for determining the position of a noteworthy point of the eye.

The steps of this method for tracking gaze direction will be explained below with reference to the embodiments of the device for tracking the direction of the gaze described above.

This method for tracking gaze direction is based on a measuring protocol that may be carried out by an optician in his shop. The position and field of the image-capturing apparatuses are predetermined in the factory at the moment of the manufacture of the device 100; 200; 300 for tracking gaze direction. Only one step of adjusting the vertical and/or horizontal position and optionally the orientation of the image-capturing apparatuses is necessary, as explained below. The method is therefore simple and rapid to implement.

More precisely, in step a), the operator positions the device for tracking gaze direction by placing the measuring support 150; 250; 350 on the pair of spectacles 400 of the wearer. This positioning implies that of the device for determining the position of a noteworthy point of the eye. It may be a question of an old pair of spectacles or of a new chosen frame, which preferably includes demonstration or corrective ophthalmic lenses. This is here achieved by pinching the frame 410 or the ophthalmic lenses 420 of the pair of spectacles 400 between the pins of the clips 131, 132, 133, 134; 231, 232, 233, 234; 331, 332, 433 for mounting the device 100; 200; 300 for tracking the direction of the gaze.

This positioning is carried out so as to ensure that the one or more light sources 110; 210; 310 of the device illuminate the eye of the wearer, that the one or more image-capturing apparatuses 120; 220; 320 capture an image of at least one portion of the eye, and so that the field of vision of the wearer is perturbed as little as possible by the presence of these elements.

In the case of the first embodiment, the position of the light sources 110 and of the image-capturing apparatuses 120 is closely related to the general shape of the frame 410 and/or of the ophthalmic lenses 420. However, it is possible to adjust empirically the relative position of the light sources and of the image-capturing apparatuses with respect to the eyes of the wearer, for example by adjusting the inclination of each measuring element 130A, 130B, 130C, 130D on the lateral arm 152 of the measuring support 150 when the means for attaching these measuring elements to the lateral arm allow it.

In the case of the second embodiment of the device according to the invention, the position of this device for tracking gaze direction with respect to the eyes of the wearer is adjusted so as to center the light sources 210 and the image-capturing apparatuses 220 on the pupil P of the eye when the wearer is looking straight ahead.

Preferably, this adjustment allows the relative position of the light sources and of the image-capturing apparatuses with respect to the eyes of the wearer to be determined.

To do this, the operator asks the wearer to look in a specific gaze direction. The point of intersection between this gaze direction and at least one of the ophthalmic lenses 420 of the pair of spectacles 400 is determined. It may for example be a question of a predetermined point of intersection.

The position of the predetermined point of intersection may optionally be noted on the ophthalmic lens. The position of this predetermined point of intersection may also be measured by another piece of equipment.

The operator adjusts the position of the one or more image-capturing apparatuses 120; 220 with respect to the position of this point of intersection.

In practice, the operator may for example ask the wearer to gaze into the distance, at the horizon. In this case, the position of the point of intersection is that of the fitting cross of the ophthalmic lens.

This case is shown in FIG. 4.

The operator then aligns the position markers 240 of the measuring support 250 with the pupil P of the eye of the wearer as the latter gazes into the distance, by virtue of the translational mobilities of the supporting ring 254 placed facing the left eye of the wearer, which mobilities are represented by the arrows F1 and F2 in FIG. 4.

A similar adjustment may be made to position the supporting ring 253 placed facing the right eye of the wearer in the second embodiment.

This amounts to aligning the center of the supporting ring 253, 254 with the center of the pupil P in the case of the second and third embodiments of the device for tracking gaze direction. This adjustment is represented by the arrows F1 and F2 in FIG. 4.

Furthermore, it is also possible to envision the operator adjusting the orientation of each supporting ring with respect to the corresponding eye of the wearer by virtue of the rotational mobilities about the vertical poles 255, 256 and about two axis that are perpendicular to each other and perpendicular to the corresponding vertical pole.

In the case of the third embodiment, the supporting ring 353 has no mobility with respect to the measuring support. It is therefore all of this measuring support 350 that may be moved slightly by the operator in order to correctly center the supporting ring 353 on the eye of the wearer.

The image-capturing apparatuses 120; 220; 320 thus positioned allow the movement of the pupils P in any direction to be followed.

In order to ensure the image-capturing apparatuses are correctly positioned, whatever the envisioned embodiment, it is possible to make provision for a step in which the user views an image obtained by the image-capturing apparatuses so as to check that at least one eye of the wearer is indeed visible in this image. The adjustment of the position of the image-capturing apparatuses is thus facilitated.

In steps b) and c), the operator for example asks the wearer to follow a protocol allowing his far vision and/or intermediate-distance vision and/or near vision to be favored.

Near vision is for example spoken of for visual tasks requiring the wearer's gaze to be fixated on a point located between 20 and 40 centimeters from the wearer.

Intermediate vision is spoken of for visual tasks requiring the wearer's gaze to be fixated on a point located between about 40 centimeters and 4 meters from the wearer.

Far vision is for example spoken of for visual tasks requiring the wearer's gaze to be fixated on a point located further than about 4 meters from the wearer.

For example, the operator asks the wearer to perform a walking activity to favor far vision and/or a reading activity to favor near vision and/or an activity working on a computer to favor intermediate-distance vision.

The image-capturing apparatuses 120; 220; 320 and the light sources 110; 210; 310 are activated during these activities, and, in step e), the gaze directions are determined by the device for tracking gaze direction in correspondence with each activity.

More precisely, in step b), the light sources 110; 210; 310 are commanded to emit light or it is ensured that the light emitted by the remote light sources or ambient light well illuminates the eye of the wearer. This command may be sent remotely or given manually by pressing a button.

In step c), the capture of at least one image by said at least one image-capturing apparatus is commanded.

The various embodiments of the device for tracking gaze direction described above comprise at least two image-capturing apparatuses that are suitable for being placed facing each eye. In step c) an image is then captured by each image-capturing apparatus 120; 220; 320, simultaneously. A stereoscopic image of the eye is therefore obtained.

The data relating to the captured images are transmitted by a wireless Wi-Fi network to the computational terminal.

In step d), processing of these images by the computational terminal therefore makes it possible to determine the three-dimensional coordinates of the noteworthy point of the eye O1 of the wearer that is identified in the images captured in step c) by each image-capturing apparatus. These coordinates are for example determined in a frame of reference associated with the image-capturing apparatuses.

The position of this noteworthy point of the eye O1 is for example determined by a triangulation calculation from these two images captured by the two image-capturing devices 120; 220; 320.

The noteworthy point of the eye, the position of which is determined in step d), is preferably a structural element of the eye, possibly the center of the pupil P of the eye, a point relating to the iris of the eye, a point on the outline of the iris, a point on the outline of the pupil, a point relating to a blood vessel of the eye, or even the external or internal canthus of the eye.

It is, in the examples described here, a question of the center of the pupil P of the eye.

According to a first embodiment of the method for determining the direction of the gaze, with reference to FIG. 5, the device for tracking gaze direction furthermore comprises a light source associated with each image-capturing apparatus.

More precisely, the device for tracking the direction of the gaze then comprises, facing each eye of the wearer, two light sources 110 and two image-capturing apparatuses 120 the positions and orientations of which are known in the mean plane of the rims 411; 412 of the frame 410 or of the ophthalmic lenses 420 mounted in the frame 410. Each light source 110 is positioned in proximity to one of the two corresponding image-capturing apparatuses 120. This configuration for example corresponds to the use of the first embodiment of the device 100 for tracking gaze direction, shown in FIG. 1, in which the measuring elements 130A, 130B, 130C, 130D each comprise a light source 110 and an image-capturing apparatus 120.

Then, in step e), for one of the eyes of the wearer,
the images of the corneal reflections RL1, RL2 of the two light sources 110 are identified in each captured image,
the three-dimensional position of the corneal reflections RL1, RL2 of the two light sources 110 are determined by triangulation calculations from these two images captured by the two image-capturing devices 120,
the three-dimensional position of the center E of the curvature of the cornea of the eye O1, which curvature is likened to a sphere, is determined depending on the position of the corneal reflections RL1, RL2 of the light sources 110,
the gaze direction DR is deduced therefrom as being the straight line joining this center E of the curvature of the cornea of the eye and the center of the pupil P.

For example, the center of the curvature of the cornea is the center of the sphere having the average radius of curvature of the cornea at the point in question. It is in particular here a question of the center of the average curvature.

More precisely, to determine the three-dimensional position of the center E of the curvature of the cornea of the eye O1, the position of the point of intersection between the two straight lines joining the entrance pupil of each image-capturing apparatus 120 and the corneal reflection RL1, RL2 of the associated light source 110 is determined. The center E of the curvature of the cornea of the eye is identified at this point of intersection.

The gaze direction is then given by the straight line joining the center of the cornea of the eye or the center of rotation of the eye and the center of the pupil of the eye. This gaze direction is for example corrected by a shift of a few degrees, typically 2 to 4 degrees, because the visual axis is anatomically shifted with respect to the gaze direction.

Figure 6:
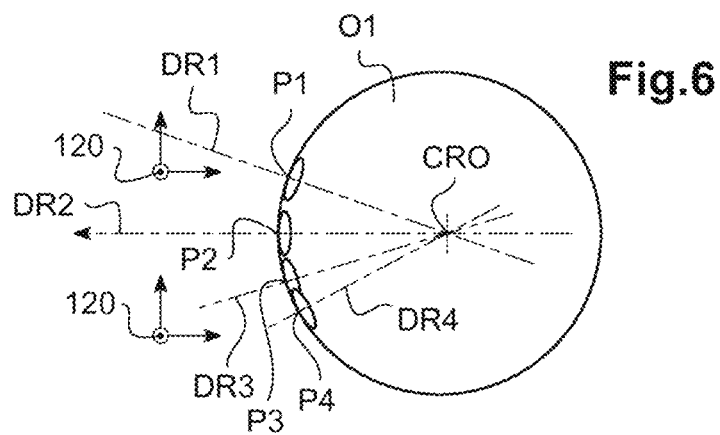

According to a second embodiment of the method for determining gaze direction, with reference to FIG. 6, the positions and orientations of the image-capturing apparatuses 120; 220; 320 are known in the mean plane of the rims 411; 412 of the frame 410 or of the ophthalmic lenses 420 mounted in the frame 410. The corneal reflections of the light sources are not identified here and the light sources 110; 210; 310 are only used to illuminate the eyes of the wearer.

This second embodiment of the method may be implemented by the three embodiments of the gaze-tracking device described above.

It may in particular be implemented when the supporting ring is used as a waveguide and illuminates the eye of the wearer.

Then, in step e), for one of the eyes of the wearer,
the three-dimensional position of the rotation center CRO of the eye O1 is determined,
the gaze direction DR1, DR2, DR3, DR4 is deduced therefrom as being the straight line joining this rotation center CRO of the eye and the pupil P1, P2, P3, P4 the position of which was determined in step d).

More precisely, according to a first variant, to determine the three-dimensional position of the rotation center CRO of the eye O1, a model of the eye is used in which the position of the rotation center CRO is determined.

To determine this model of the eye, it is possible for example to identify the image of the pupil P1, P2, P3, P4 of the eye O1 in a plurality of pairs of images of the eye, which images are captured simultaneously by the two image-capturing apparatuses 120; 220; 320 for various gaze directions of the wearer, to determine the position of the pupils P1, P2, P3, P4 of the eye O1 in three dimensions for these various directions of the gaze and to determine the model of the eye as being a sphere passing through the points having the positions of the pupils P1, P2, P3, P4 of the eye for these various directions of the gaze. The position of the rotation center CRO is then determined as being the center of this sphere.

According to a second variant, to determine the three-dimensional position of the rotation center CRO of the eye O1, it is measured by virtue of a piece of equipment and according to a method known to those skilled in the art, for example using the Essilor "Visioffice" device. This step corresponds to a prior calibrating step.

Figure 7:
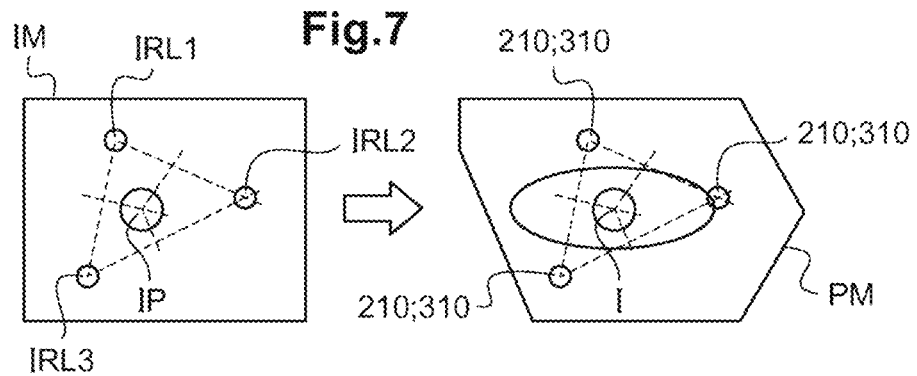

According to a third embodiment of the method for determining gaze direction, with reference to FIG. 7, the device 200; 300 for tracking gaze direction includes at least three light sources 210; 310 facing the eye of the wearer. This is the case of the second and third embodiments. The positions of these light sources 210; 310 with respect to the image-capturing apparatuses are initially unknown.

They are preferably also as little off-center as possible with respect to the eye of the wearer without perturbing his vision.

It is not useful here to know the positions and orientations of the image-capturing apparatuses.

In a first substep, the relative position of the light sources 210; 310 with respect to the frame 410 or with respect to a reference point, for example the far-vision reference point of the ophthalmic lens, i.e. the fitting cross, is learnt.

For this purpose, the position of the light sources with respect to the frame 410 or with respect to a reference point, such as the fitting cross of the ophthalmic lens for example, is adjusted, or an image of the entirety of the frame 410 and of the device 200; 300 for tracking gaze direction is captured.

It is also possible to use the capacity of the sensor of the image-capturing apparatus to detect the near infrared to instantaneously detect each of the light sources by activating them in turn.

The apparent position of the eye rotation center CRO and of the apparent radius of the eye in the field of the image-capturing apparatus are calculated by virtue of a model of the eye of the wearer similar to that described above, i.e. by modelling the eye as a sphere passing through the positions of the pupils of the wearer, which positions are determined from the positions thereof identified in various pairs of images corresponding to different gaze directions.

This may be done by capturing images, in particular stereoscopic images, during a learning sequence carried out on the wearer, by asking him to turn his eyes randomly, or by using sequences of images acquired during the protocol described above allowing the far vision and/or intermediate-distance vision and/or near vision of the wearer to be favored.

Next, for a pair of given simultaneous images, the image of the pupil IP of the eye is identified and the three-dimensional position of the center of this pupil is determined by a triangulation calculation.

The images IRL1, IRL2, IRL3 of the corneal reflections of the light sources 210; 310 and of the noteworthy point of the eye, here the image of the center of the pupil IP, are identified in these images IM (FIG. 7) and the three-dimensional position of these corneal reflections and of the center of the pupil are determined by a triangulation calculation for each pair of captured images.

Analysis of the relative position of the pupil with respect to the CRO allows the position of the center of the cornea to be estimated. A simplified model in which the eye rotation center, the center of the cornea and the center of the pupil are aligned is for example used. By virtue of median values, or values measured specifically on the wearer, the following quantities are known: the radius of the eye, the corneal radius and the actual position of the pupil, which is different from the position of its image through the cornea. Thus, it is possible to deduce therefrom the apparent position of the center of the cornea in the image captured by the image-capturing apparatus.

This makes it possible to calculate the spherical coordinates of the center of the pupil and of the corneal reflections in the frame of reference of the cornea, then to calculate a "barycentric system" relating the spherical coordinates of the center of the pupil in the frame of reference of the cornea to the corneal reflections. The relative position of the center of the pupil and of the corneal reflections is thus determined.

The barycentric coordinates of the image of the pupil of the eye with respect to the corneal reflections are then transferred to a frame of reference associated with the frame or with the ophthalmic lenses, in order to determine the position of the center of the pupil in the latter frame of reference.

In a simplified case, in particular corresponding to the case where the angles between the corneal reflections and the gaze direction are small, for example smaller than 10 degrees of angle, this transfer of the barycentric coordinates comprises a calculation based on a bijection between the coordinates of the pupil in the frame of reference of the image-capturing apparatus and the point of intersection of the gaze direction with a surface associated with the ophthalmic lens in the frame of reference of this ophthalmic lens.

In a more complex case, it is necessary to know the apparent position of the eye, and in particular of the surface of the cornea, in order to be able to estimate the actual angular deviation between the pupil and the corneal reflections.

From the position of the eye rotation center and from the identification of the image of the pupil in the captured image, the polar coordinates of the center of the pupil and of the corneal reflections of the light sources are determined in the frame of reference of the cornea.

In the frame of reference of the cornea, the actual distances between the corneal reflections are determined, for example in the way described in the document by Arantxa Villanueva, Juan J. Cerrolaza and Rafael Cabeza (2008), entitled "Geometry Issues of Gaze Estimation", in "Advances in Human Computer Interaction", Shane Pinder (Ed.), ISBN: 978-953-7619-15-2, InTech, DOI: 10.5772/5911.

The direction of the gaze of the wearer in the frame of reference of the frame or of the ophthalmic lenses is deduced from the position of the light sources in this frame of reference and from the relative position of the noteworthy point and of the corneal reflections.

This is for example done by determining, via an optimization calculation, the point of intersection I (FIG. 7) of the direction of the gaze on the mean plane PM of the rim of the frame or of the ophthalmic lens from the relative position, determined beforehand, of the center of the pupil and of the corneal reflections, and from the coordinates of the light sources 210, 310 in the frame of reference of the frame or of the ophthalmic lenses. The gaze direction is then the straight line joining the pupil P of the eye to the determined point of intersection.

In the case where provision is made for only a single image-capturing apparatus in front of each eye of the wearer, the image of the noteworthy point is identified, in step d), in the captured image. Next, taking into account the known relative position of the image-capturing apparatus with respect to the eye of the wearer and a model of this eye in which the position of the eye rotation center is known, the position of the noteworthy point is determined in the frame of reference of the image-capturing apparatus and the direction of the gaze of the wearer is deduced therefrom. The operator may also ask the wearer to fixate on a target, the position of which is moreover determined in the frame of reference of the image-capturing apparatus. The gaze direction is then determined to be the straight line joining the eye rotation center and the target.

In the case where the noteworthy point the position of which is determined in step d) is not the center of the pupil, it is possible to envision deducing the position of the center of the pupil from a model of the eye and from the position of this noteworthy point. The various embodiments of the methods described above are then implemented in the same way.

It is also possible to envision in this case estimating the angular deviation of the gaze direction with respect to a predetermined reference gaze direction for which the position of the noteworthy point of the eye is known.

Specifically, knowing a reference gaze direction and the corresponding reference angular position of the associated noteworthy point, an angular deviation between the gaze direction and the noteworthy point in question is determined. It is subsequently assumed that this angular deviation remains constant.

For example, the noteworthy point may correspond to a blood vessel located at −15 degrees of angle in the sagittal plane and 23 degrees of angle in the plane tangental to the gaze direction. Continuously tracking the position of this noteworthy point and calculating the spherical coordinates of this noteworthy point in a frame of reference associated with the eye rotation center allows the gaze direction to be immediately deduced, assuming that the angular position of this noteworthy point with respect to the gaze direction remains constant.

In the case where the device for tracking gaze direction is arranged so that the light sources and image-capturing apparatuses are placed on the exterior of the pair of spectacles, i.e. such that the ophthalmic lens is placed between the image-capturing apparatus and the eye of the wearer, prismatic effects introduced by the presence of this ophthalmic lens are taken into account when determining the positions of the corneal reflections or of the noteworthy point of the eye.

This is in particular the case when the one or more light sources are remote, i.e. not mounted on the pair of spectacles with the one or more image-capturing apparatuses.

It is then possible to determine the real gaze directions, not refracted through the ophthalmic lenses, from the geometry of this lens and the power distribution of this lens. This is also possible in the case where the ophthalmic lens is afocal.

Once a plurality of directions of the gaze of the wearer have been determined according to one of the embodiments of the method for determining the direction of the gaze described above, for each direction DR of the gaze, its point of intersection with a predetermined surface relating to the frame and/or to the ophthalmic lens of the wearer is determined, a zone of use of the ophthalmic lens intended to equip the wearer is determined depending on said points of intersection.

It is thus possible to determine at least one zone of use of this ophthalmic lens.

In practice, the coordinates of the intersection of the direction of the gaze with the mean plane of the corresponding rim 411, 412 of the frame 410 or with the mean surface of the corresponding ophthalmic lens 420 is determined.

The mean surface of the ophthalmic lens is defined as the surface equidistant at every point from the front and back faces of the lens.

The predetermined surface taken into account may also be one of the front or back faces of the ophthalmic lens. It may also be a question of the mean plane of the ophthalmic lens, which plane is defined as being the plane containing the points statistically closest to the mean surface of this ophthalmic lens.

In the case of the third embodiment of the method for determining gaze direction, it is not necessary to determine the coordinates of this intersection since the point of intersection I (FIG. 7) of the direction of the gaze on the mean plane PM of the rim of the frame or of the ophthalmic lens has already been determined from the relative position, determined beforehand, of the center of the pupil and of the corneal reflections, and from the coordinates of the light sources 210, 310 in the frame of reference of the frame or of the ophthalmic lenses, for example via an optimization calculation. The points of the zone of use may then be identified directly from the determined points of intersection. They may also be deduced from these points of intersection while taking into account a correction representing the fact that the light sources are not, in a general case, positioned in a plane parallel to the mean plane of the rim of the frame or of the ophthalmic lens in question.

The computational terminal uses this information to design the new ophthalmic lenses intended for the wearer.

It is for example a question of determining the position and extent of the zones of use of each ophthalmic lens corresponding to near vision, intermediate-distance vision or to far vision. It is then a question of mapping those zones of the ophthalmic lens which are used by the wearer in near vision and those used in far vision.

These zones of use are determined depending on the position of the points of intersection with the predetermined plane of the gaze directions determined from the images captured during the visual tasks ensuring the wearer was using his near vision, intermediate-distance vision, or far vision.

A zone of use may be determined so as to encompass all the determined points of intersection corresponding to the visual task in question.

This zone of use may have a predefined shape. It may extend so that its outline passes at a preset threshold distance from each point of intersection.

It may be a question of an ellipse or a rectangle that contains all or a percentage of the determined points of intersection. Preferably, the outline of the zone of use surrounds at least 95% of the determined points of intersection.

It is for example a question of defining a zone encompassing all the points of intersection corresponding to a given visual task.

The zones of use may be limited by the geometry of each frame. They may depend on the qualities of the lens that it is desired to exploit therethrough.

For example, for a progressive ophthalmic lens, without limitation on the frame, the zones of use for near and far vision could have a vertical angular amplitude of 60 degrees and a horizontal angular amplitude of 60 degrees.

The computational terminal may also be programmed to deduce other optical design parameters of the ophthalmic lens from the information on the gaze directions. The vertical distance between the average gaze direction during a far-vision activity and the average gaze direction during a near-vision activity may be determined, so as to allow a progressive-addition ophthalmic lens to be designed in which the distance between the fitting cross and the center of the near-vision zone is identical to this determined vertical distance.

The infrared light source may be of small size (it may for example measure about 0.2 millimeters by 0.2 millimeters) and be positioned to form an image in the central visual field, whether this be by direct illumination or via a waveguide, and it may optionally be impossible or very difficult to see, and thus make it possible to neither decrease the visual comfort of the wearer, nor introduce parasitic objects into his field of vision.

It is possible to envision the supporting ring not being maintained by a horizontal bar but instead being positioned directly on the ophthalmic lens or frame via a sucker-based maintaining system, by magnets positioned on either side of the ophthalmic lens or frame, or even by weakly adhesive repositionable elements. It is also possible to envision maintenance by capillary action (droplet of water, magic patches)

or direct dry bonding via micro/nano surface structuring, for example with carbon nanowires.

The invention claimed is:

1. A device for determining the position of a noteworthy point of an eye (O1) of a wearer equipped with a vision frame including at least two rims and/or two ophthalmic lenses, the device comprising:
   at least one image-capturing apparatus, and
   positioning means for positioning the image-capturing device with respect to said vision frame, in such a way that, when said vision frame is placed in useful position on the head of the wearer, the image-capturing apparatus is suitable for capturing an image of this eye (O1) of the wearer, the positioning means comprising a measuring support that is equipped with a horizontal bar and two lateral arms, and two clips belonging to said horizontal bar and suitable for interacting with an upper portion of the rims or ophthalmic lenses of the vision frame, and two clips that are each placed at the end of one of the lateral arms and suitable for interacting with a lower portion of the rims or of the ophthalmic lenses of the vision frame, and
   means for determining the position of a noteworthy point of the eye (O1) of the wearer from said at least one image of the eye (O1) of the wearer which was captured by the image-capturing apparatus.

2. The device as claimed in claim 1, wherein provision is furthermore made for at least one light source arranged so as to illuminate at least one eye (O1) of the wearer, the image captured by the image-capturing apparatus then comprising an image of at least this eye (O1) of the wearer illuminated by said light source.

3. The device as claimed in claim 2, wherein said positioning means are suitable for positioning said device with respect to said vision frame in such a way that, when said vision frame is placed in useful position on the head of the wearer, the light source is suitable for illuminating the eye (O1) of the wearer.

4. The device as claimed in claim 2 wherein, the vision frame comprising at least one frame temple for its installation on the head of the wearer, the positioning means are suitable for interacting with this vision frame, such that each light source and each image-capturing apparatus is placed on the side of the vision frame on which said frame temple extends.

5. The device as claimed in claim 2 wherein, said vision frame including at least one rim and/or one ophthalmic lens, each light source and each image-capturing apparatus is arranged such that it is placed facing said rim or said ophthalmic lens of the vision frame when the positioning means are interacting with said vision frame.

6. The device as claimed in claim 2 wherein, said vision frame including at least two rims and/or two ophthalmic lenses, provision is made for at least two light sources and two image-capturing apparatuses, which are arranged such that at least one of the two light sources and one of the two image-capturing apparatuses is placed facing each rim or each ophthalmic lens of the vision frame when the positioning means are interacting with this vision frame.

7. The device as claimed in claim 6, wherein provision is made for four image-capturing apparatuses that are arranged such that two image-capturing apparatuses are placed facing each rim or each ophthalmic lens of the vision frame when the positioning means are interacting with said vision frame.

8. The device as claimed in claim 2 wherein each light source is a light-emitting diode emitting in the domain of the infrared wavelengths.

9. The device as claimed in claim 1 wherein said positioning means are positioning means that make the device removable while permitting the device to be mounted on the vision frame and this device to be demounted.

10. The device as claimed in claim 1, wherein each light source and each image-capturing apparatus is borne by one of the lateral arms of the measuring support.

11. The device as claimed in claim 1, wherein said measuring support furthermore comprises a supporting ring that is mounted on said horizontal bar and supports said at least one light source and said at least one image-capturing apparatus.

12. The device as claimed in claim 11, wherein said supporting ring is mounted on said horizontal bar so as to be translationally movable along an axis parallel to the straight line joining the two clips of the horizontal bar and/or translationally movable along an axis perpendicular to this straight line.

13. The device as claimed in claim 12, wherein said supporting ring is open or closed.

14. The device as claimed in claim 11 wherein said supporting ring is open or closed.

15. The device as claimed in claim 1 wherein said measuring support furthermore includes at least one waveguide guiding the light emitted by said light source.

16. A device for tracking the gaze direction of a wearer equipped with a vision frame, comprising a device for determining the position of a noteworthy point of an eye (O1) of the wearer as claimed in claim 1 and means for determining the gaze direction of the wearer depending on the position of this noteworthy point of the eye (O1).

17. A method for determining the position of a noteworthy point of at least one eye (O1) of a wearer equipped with a vision frame, by means of a device for determining the position of a noteworthy point of the eye (O1) of a wearer as claimed in claim 1 including at least one image-capturing apparatus that is arranged to be facing this eye (O1) of the wearer, comprising the following steps:
   a positioning step of positioning the device for determining the position of a noteworthy point of the eye (O1) of the wearer with respect to the vision frame of the wearer,
   a capturing step of capturing at least one image of the eye (O1) of the wearer with the image-capturing apparatus of said tracking device, and
   a determination step of determining the position of the noteworthy point of the eye (O1) from the captured image.

18. The method for determining the position of a noteworthy point of at least one eye (O1) of a wearer as claimed in claim 17, wherein, in said positioning step, the device for determining the position of a noteworthy point of the eye (O1) of the wearer is positioned with respect to the vision frame of the wearer such that said at least one image-capturing apparatus is suitable for capturing an image of the eye (O1) of the wearer.

19. The method as claimed in claim 17 wherein, the device for determining the position of a noteworthy point of the eye (O1) including at least two image-capturing apparatuses that are arranged so as to be facing the eye (O1) of the wearer, in said determination step, the position of the noteworthy point of the eye (O1) is determined via a triangulation calculation from two images that are captured simultaneously by the two image-capturing devices.

20. A method for determining the gaze direction of at least one eye (O1) of a wearer equipped with a vision frame, by means of a device for tracking gaze direction which includes i) a device for determining the position of a noteworthy point of an eye (O1) of a wearer equipped with a vision frame including at least two rims and/or two ophthalmic lenses, comprising:

at least one image-capturing apparatus, and positioning means for positioning the image-capturing device with respect to said vision frame, in such a way that, when said vision frame is placed in useful position on the head of the wearer, the image-capturing apparatus is suitable for capturing an image of this eye (O1) of the wearer, the positioning means comprising a measuring support that is equipped with a horizontal bar and two lateral arms, and two clips belonging to said horizontal bar and suitable for interacting with an upper portion of the rims or ophthalmic lenses of the vision frame, and two clips that are each placed at the end of one of the lateral arms and suitable for interacting with a lower portion of the rims or of the ophthalmic lenses of the vision frame, and means for determining the position of a noteworthy point of the eye (O1) of the wearer from said at least one image of the eye (O1) of the wearer which was captured by the image-capturing apparatus, and ii) means for determining the gaze direction of the wearer depending on the position of this noteworthy point of the eye (O1), the at least one image-capturing apparatus arranged to be facing this eye (O1) of the wearer, the method comprising the following steps:

a step of determining the position of a noteworthy point of at least one eye (O1) of the wearer using the determining method of claim 17, and a step of determining the gaze direction of the wearer depending on the position of this noteworthy point of the eye (O1).

21. The method as claimed in claim 20, wherein, the noteworthy point of the eye (O1) the position of which is determined in said determination step being the center of the pupil of the eye (O1) or a point on the outline of the pupil of the eye (O1), in said step of determining the position of a noteworthy point of at least one eye (O1) of the wearer, the position of a rotation center of the eye (O1) or the center of curvature of the cornea is determined and the gaze direction is deduced therefrom as being the straight line joining this rotation center or this center of the curvature of the cornea of the eye (O1) and the center of the pupil or a point on the outline of the pupil.

22. The method as claimed in claim 20, wherein, the device for tracking gaze direction includes at least three light sources that are facing the eye (O1) of the wearer and, in said determination step:

the corneal reflections of the three light sources and the image of the noteworthy point of the eye (O1) are identified in the image captured in said capturing step, the relative position of the noteworthy point and of the corneal reflections is determined, and in said step of determining the position of a noteworthy point of at least one eye (O1) of the wearer:

the direction of the gaze of the wearer in a predetermined frame of reference is deduced from the position of the light sources in this predetermined frame of reference and from the relative position of the noteworthy point and of the corneal reflections.

23. A method for determining a zone of use of an ophthalmic lens by a wearer of a vision frame comprising at least one frame and/or one ophthalmic lens, wherein a plurality of directions of the gaze of this wearer are determined using the method for determining the direction of the gaze as claimed in claim 20, for each direction of the gaze, its point of intersection with a predetermined surface relating to the frame and/or to the ophthalmic lens of the wearer is determined, and said zone of use is determined depending on said points of intersection.

* * * * *